(12) United States Patent
Barrier et al.

(10) Patent No.: US 8,696,651 B2
(45) Date of Patent: Apr. 15, 2014

(54) MANIPULATOR WITH DECOUPLED MOVEMENTS, AND APPLICATION TO INSTRUMENTS FOR MINIMALLY INVASIVE SURGERY

(75) Inventors: Pascal Barrier, Annecy (FR); Jérémy Ollagnier, Annecy le Vieux (FR); Gérard Gautier, Cran Gevrier (FR)

(73) Assignee: Dexterite Surgical, Annecy (FR)

( * ) Notice: Subject to any disclaimer, the term of this patent is extended or adjusted under 35 U.S.C. 154(b) by 775 days.

(21) Appl. No.: 12/864,899

(22) PCT Filed: Jan. 31, 2009

(86) PCT No.: PCT/IB2009/050390
§ 371 (c)(1),
(2), (4) Date: Jul. 28, 2010

(87) PCT Pub. No.: WO2009/095893
PCT Pub. Date: Aug. 6, 2009

(65) Prior Publication Data
US 2010/0331860 A1 Dec. 30, 2010

(30) Foreign Application Priority Data
Jan. 31, 2008 (FR) .................... 08 50612

(51) Int. Cl.
*A61B 17/00* (2006.01)
(52) U.S. Cl.
USPC ............................................. 606/1; 606/130
(58) Field of Classification Search
USPC .................................................. 606/1, 130
See application file for complete search history.

(56) References Cited

U.S. PATENT DOCUMENTS

| | | | |
|---|---|---|---|
| 5,797,900 A | 8/1998 | Madhani | |
| 2003/0033024 A1 | 2/2003 | Sunaoshi | |
| 2003/0109957 A1 | 6/2003 | Sanchez | |
| 2006/0020287 A1 | 1/2006 | Lee | |
| 2006/0206101 A1* | 9/2006 | Lee .................................. | 606/1 |
| 2007/0137372 A1* | 6/2007 | Devengenzo et al. ..... | 74/490.01 |
| 2007/0208375 A1* | 9/2007 | Nishizawa et al. ........... | 606/205 |

FOREIGN PATENT DOCUMENTS

| | | |
|---|---|---|
| FR | 2713129 A1 | 6/1995 |
| FR | 2876271 A1 | 4/2006 |
| WO | 2005046500 A1 | 5/2005 |
| WO | 2006005061 A2 | 1/2006 |

\* cited by examiner

*Primary Examiner* — Bill Thomson
*Assistant Examiner* — Jeffrey Lipitz
(74) *Attorney, Agent, or Firm* — William H. Eilberg

(57) ABSTRACT

A manipulator includes a main arm, of which the proximal end bears a drive, and a proximal manipulation structure, and of which the distal end bears a controlled distal structure that may itself bear a surgical tool. The main arm passes through a surgical trocar. The proximal manipulation structure includes two opposed contact zones and stress sensors positioned in a central zone between the two opposed contact zones. The stress sensors operate the drive as a function of the stresses applied to the contact zones in order to produce the pivoting and rotating movements of the surgical tool with respect to the main arm. This ensures that there is optimal decoupling of the movements in the various degrees of freedom, thus making it easier to obtain movements through stressing operations that are natural to the operating surgeon.

14 Claims, 17 Drawing Sheets

MANIPULATOR WITH DECOUPLED MOVEMENTS, AND APPLICATION TO INSTRUMENTS FOR MINIMALLY INVASIVE SURGERY

TECHNICAL FIELD OF THE INVENTION

The present invention concerns guide and manipulator devices enabling the movements of a manipulator instrument situated inside an operating area to be controlled from outside the operating area.

The invention concerns in particular a guide and manipulator device of this kind for controlling a surgical instrument in minimally invasive surgical applications carried out endoscopically.

In recent years, minimally invasive endoscopic surgery has expanded considerably.

For this purpose essentially two types of surgical instrument guide and manipulator device have been designed.

In the first type of guide and manipulator device, described for example in the document FR 2 713 129 A or FR 2 876 271 A, the surgical instrument is placed at the end of a portable manipulator essentially having a main arm with a proximal end and a distal end. The proximal end of the arm carries a proximal manipulator structure adapted to generate movement instructions as a function of forces applied by a hand of an operator. A distal controlled structure is carried by the distal end of the main arm and is mobile relative to said distal end of the main arm with at least two degrees of freedom in transverse pivoting and possibly one degree of freedom in axial rotation. Movements applied by the operator to the proximal manipulator structure are transmitted by transmission means in the main arm and reproduced by the distal controlled structure.

During a surgical operation, the main arm is passed through the skin of a patient, the proximal manipulator structure remaining outside the body of the patient, the distal controlled structure then being inside the body of the patient to perform the surgical action.

In the device from the document FR 2 713 129 A, the proximal manipulator structure has contact areas for two fingers of an operator to bear on, the contact areas being disposed at the end of a lever articulated to the proximal end of the main arm by a ball-joint. The distal controlled structure is disposed at the end of a distal lever itself articulated to the distal end of the main arm by a second ball-joint. The two ball-joints are mechanically linked to each other so that the distal ball-joint reproduces the rotation of the proximal ball-joint.

A first drawback of this device is the difficulty of performing a precise surgical action. It is found difficult to apply to the proximal manipulator structure forces enabling precise production of pure rotation movements or pure translation movements of the distal controlled structure.

A second drawback of this device is the relatively small relative angular movement possible in movements in pivoting of the distal controlled structure about a transverse axis.

The same drawbacks are also found in the device described in the document FR 2 876 271 A.

That document further describes an embodiment in which the proximal manipulator structure is offset away from the main arm and the transmission of movement between the proximal manipulator structure and the distal controlled structure is effected via drive means supplied with power by an external power supply.

In the second type of guide and manipulator device for surgical instruments as described for example in the document U.S. Pat. No. 5,797,900 A, the surgical instrument is actuated by a remote-controlled robot. A master arm, operable by an operator, is completely separate from a slave arm that carries the surgical instrument. The master arm and the slave arm are usually articulated arms having at least six degrees of freedom of movement; the master arm is provided with sensors detecting the forces applied to it, and mechanical forces are applied to the slave arm by motorized actuators that respond to the signals produced by the master arm sensors. Thus the connection between the master arm and the slave arm is provided by electrical signals and the robot is generally placed at a distance from the master arm.

Another example of a remote-controlled manipulator of this second type of guide and manipulator device is described in the document US 2003/0109957 A1. This document describes in more detail a proximal manipulator structure in the form of a handgrip connected to a fixed support by five successive articulations each provided with movement sensors for remotely controlling a slave arm carrying a surgical instrument. Starting from the fixed support, a master shoulder rotation commands lateral pivoting of the slave arm about the trocar in a first longitudinal plane, a master elbow rotation commands lateral pivoting of the slave arm about the trocar in a second longitudinal plane, a master forearm axial translation commands axial translation of the slave arm in the trocar, a master wrist axial rotation commands axial rotation of the slave arm in the trocar and, finally, transverse rotation of the handgrip commands rotation of the slave arm. Except for the wrist transverse rotation sensor, all the movement sensors are situated in connecting areas that are clearly separated from the wrist. This device with successive articulations is not applicable to a portable manipulator because the slave arm must then be held mechanically by the proximal manipulator structure, and the articulations do not allow this. Furthermore, in the above document, the surgical instrument is not mobile relative to the slave arm in orientation and in rotation.

Because of their complexity, such remote-controlled manipulators are bulky and costly and have high maintenance costs. The operator actuates the master arm at a position far from the patient, with the result that the operator cannot act to administer rapid emergency medical treatment to the patient. Also, the bulk of the system necessitates lengthy preparation and total reorganization of the operating theatre and working procedures.

It will also be noted that these documents describe a distal controlled structure in which the surgical tool cannot execute an axial rotation movement about its own axis, as is sometimes necessary in surgical procedures, in which case the surgical procedures necessitate the intervention of a plurality of movements on different axes, which movements must be simultaneous and synchronized, and this necessitates relatively complex computer means and further complicates the device.

SUMMARY OF THE INVENTION

The problem addressed by the present invention is to design a new type of manipulator that makes it possible to make surgical actions more precise without necessitating a large overall size and a large investment.

The invention aims in particular to make surgical actions more precise without recourse to a remote-controlled robot.

The invention stems from the observation that known portable manipulators do not discriminate effectively the various movement stresses applied to the proximal manipulator structure. In particular, a stress for relative pivoting about a transverse axis applied to the proximal manipulator structure generally induces not only a similar relative pivoting movement about a transverse axis of the distal controlled structure relative to the main arm but also a movement of overall pivoting and of overall axial translation of the main arm itself relative to the body of the patient.

To avoid these drawbacks, the invention proposes a manipulator including:

a main arm having a proximal end and a distal end, a proximal manipulator structure carried by the proximal end of the main arm, to which it is connected by a connecting structure, having at least two opposite contact areas conformed to have two opposite parts of a hand of an operator bear on them, and including stress sensors adapted to generate movement instructions as a function of the stresses applied by the hand of the operator, a distal controlled structure, carried by the distal end of the main arm and mobile relative to said distal end with at least two degrees of freedom in transverse relative pivoting and one degree of freedom in axial rotation on itself, drive means supplied with power by a power supply and adapted to generate movements as a function of movement instructions received from the proximal manipulator structure, and mechanical transmission means accommodated in the main arm, mechanically coupled to the drive means and adapted to transmit movements of the drive means to the distal controlled structure to generate the movements of the distal controlled structure as a function of the movement instructions coming from the proximal manipulator structure, wherein:

the connecting structure is disposed in an intermediate area between the opposite contact areas of the proximal manipulator structure, and stress sensors are disposed in said connecting structure and adapted to generate the instructions for movement of the distal controlled structure relative to the main arm with at least two degrees of freedom of movement as a function of the stresses detected in said connecting structure.

Because stress sensors are disposed and arranged in such a manner as to generate instructions for movement of the distal controlled structure as a function of the stresses present in and detected in a connecting structure situated between the two opposite contact areas, it is possible to discriminate movement stresses applied to the proximal manipulator structure according to the different degrees of freedom of the manipulator.

According to a first possibility, the connecting structure includes an articulation and the sensors are displacement sensors sensitive to the relative displacement of the main arm and the proximal manipulator structure on either side of the articulation.

According to a second possibility, the connecting structure is an elastically deformable structure and the sensors are strain gauges sensitive to deformation of the connecting structure.

In a first practical embodiment:

the proximal manipulator structure is offset radially away from the longitudinal axis of the main arm, the opposite contact areas are, in a median position, aligned in a direction at an angle of approximately 45° to the longitudinal axis of the main arm, and the stress sensors disposed in the connecting structure are adapted to generate the instructions for movement of the distal controlled structure in accordance with the two degrees of freedom in relative transverse pivoting and the one degree of freedom in axial rotation on itself.

As a result, centered relative pivoting stresses applied to the proximal manipulator structure have very little effect on other possible movements of the manipulator, notably movements of overall translation and overall pivoting of the main manipulator arm. This ensures good discrimination of the possible movements of the manipulator according to its different degrees of freedom whilst all movements are commanded by application of stresses to only two opposite contact areas of the proximal manipulator structure.

In a second practical embodiment:

the connecting structure is centered on the longitudinal axis of the main arm, the stress sensors disposed in the connecting structure are adapted to generate the instructions for movement of the distal controlled structure in accordance with the two degrees of freedom of movement in relative transverse pivoting, and the movements of axial rotation on itself of the distal controlled structure are commanded by the movement instructions generated by an additional stress sensor carried by the proximal manipulator structure and adapted to be actuated by a finger of the user acting on the proximal manipulator structure.

As a result, discrimination of the possible movements of the manipulator according to its different degrees of freedom is further improved.

The manipulator defined above is a portable unit that the operator can hold in his hand during a surgical operation. Such a manipulator may advantageously further include an intermediate bearing member for the main arm in which the main arm can slide axially and which can pivot with a spherical overall pivoting movement. This facilitates guiding the distal controlled structure for total control of its positioning relative to an intervention area.

The main arm may preferably further have a movement of overall axial rotation relative to the intermediate bearing member.

In practice, a manipulator as defined above may have a distal controlled structure that comprises a distal support articulated to the end of the main arm, adapted to oscillate on either side of the longitudinal axis of the main arm in relative pivoting movement with two degrees of freedom about intersecting transverse axes. The articulated distal support carries a tool-holder rotary shaft adapted to turn in axial rotation on itself on the distal support. This imparts to the surgical tool placed on the manipulator all the required degrees of relative movement.

In all cases, the stress sensors, the drive means and the mechanical transmission means may advantageously be adapted so that:

a stress for centered relative pivoting applied to the proximal manipulator structure produces similar relative pivoting of the distal support of the distal controlled structure, and a stress for axial rotation on itself applied to the proximal manipulator structure produces similar relative axial rotation of the tool-holder rotary shaft.

To carry out certain surgical actions, the distal controlled structure must be adapted to reproduce easily relative pivoting movements of large amplitude about two intersecting transverse axes. Thus a second aspect of the invention proposes a new distal controlled structure making it possible both to reproduce faithfully the relative pivoting movements and to increase the maximum amplitude of such movements relative to the capacities offered by known devices, whilst allowing axial rotation movements on itself of a tool carried by the distal controlled structure.

To provide this great amplitude of movements of relative pivoting of the distal controlled structure relative to the main arm, the invention proposes a distal controlled structure that includes:

- at the distal end of the main arm, a female articulation member with a hemispherical distal cavity,
- an articulated distal support a male articulation member in the form of a hollow hemispherical flange having a hemispherical external surface and an interior void wide open toward its base,
- the male articulation member being engaged in the distal hemispherical cavity of the female articulation member with its interior void oriented toward the distal hemispherical cavity,
- a plurality of control lines extending in the main arm, mechanically coupled to the drive means and engaged at the periphery of the hemispherical external surface of the male articulation member to command pivoting thereof by traction on the control lines,
- a tool-holder rotary shaft in the form of an output shaft rotatably mounted on a radial bearing of the male articulation member and carrying a tool or a tool-holder,
- an input shaft mounted to rotate in an axial bearing of the female articulation member and engaged longitudinally in the main arm, and
- a homokinetic transmission that connects the input shaft to the output shaft, allowing movements of transverse pivoting of the male articulation member in the female articulation member.

This produces a distal controlled structure that itself has two degrees of freedom in relative pivoting about intersecting transverse axes and imparting to a surgical tool that it carries a degree of freedom in axial rotation on itself, these relative movements of pivoting and rotation on itself being totally independent of each other, and the relative pivoting movements having amplitudes of the order of 70° on either side of the longitudinal axis of the main arm.

A distal controlled structure of this kind may be used on a manipulator independently of the presence or the absence of the particular movement discrimination means referred to above.

An ongoing concern is to produce a portable manipulator that is both less costly and easily manipulated. Thus a third aspect of the invention further aims to reduce the weight and the overall size of such a manipulator.

To this end, the invention proposes a design of such a manipulator in which the main shaft is slidably engaged in a passage of a surgical trocar or a support arm forming an intermediate bearing member, the surgical trocar or the support arm having connecting means with sliding contacts for transmitting electrical power and control and monitoring signals between the main arm and an external power supply and processing system.

As a result, the power supply and processing system may be offset from the manipulator itself, and have no effect on its weight and overall size in the vicinity of the operating area.

Such a trocar or support arm with sliding contacts may be used independently of the presence or the absence of the other means described above for discriminating movement or for increasing the amplitude of relative pivoting.

BRIEF DESCRIPTION OF THE DRAWINGS

Other objects, features and advantages of the present invention will emerge from the following description of particular embodiments given with reference to the appended figures, in which.

DESCRIPTION OF PREFERRED EMBODIMENTS

Figure 1:
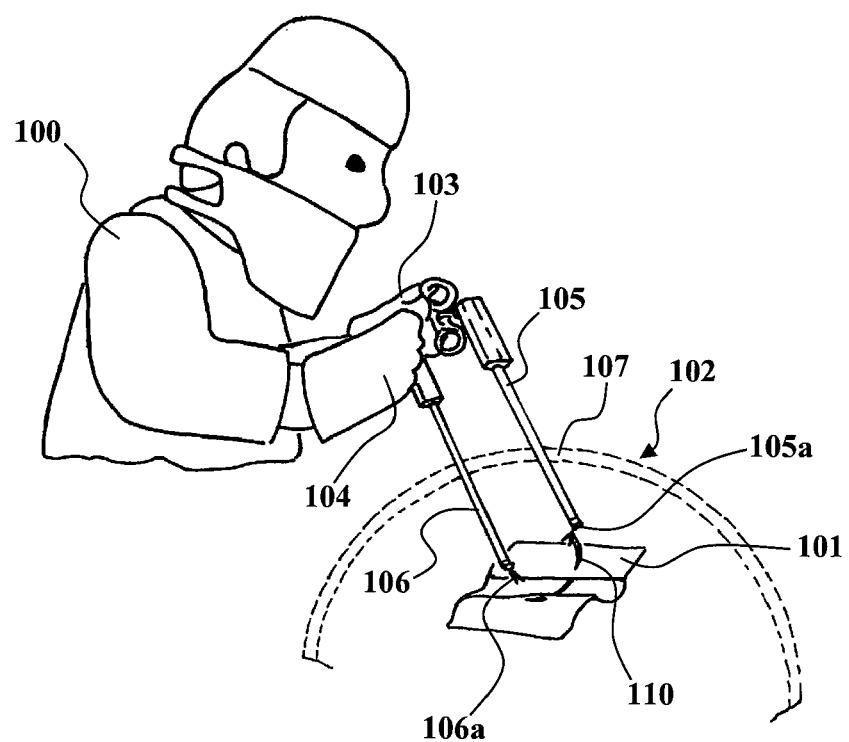
FIG. 1 shows diagrammatically an operator actuating two manipulators of the present invention to carry out a surgical operation.

As shown in FIG. 1, during a minimally invasive surgical operation, an operator 100 has to act on tissue 101 situated inside the body 102 of a patient. The operator manipulates with his hands 103 and 104 two manipulators 105 and 106 for effecting a suture, for example, by passing a curved needle 110 through the tissue 101.

Each of the two manipulators 105 and 106 passes through the skin 107 of the body 102 of the patient, a distal portion of each of the manipulators 105 and 106 thus being situated inside the body 102 of the patient, while a proximal portion is outside the body so that it can be manipulated by the operator 100.

The invention aims to enable the operator 100 to execute natural and simple movements of his hands 103 and 104 to execute the necessary movements of the respective surgical tools 105a and 106a disposed at the distal ends of the respective manipulators 105 and 106.

Figure 2:
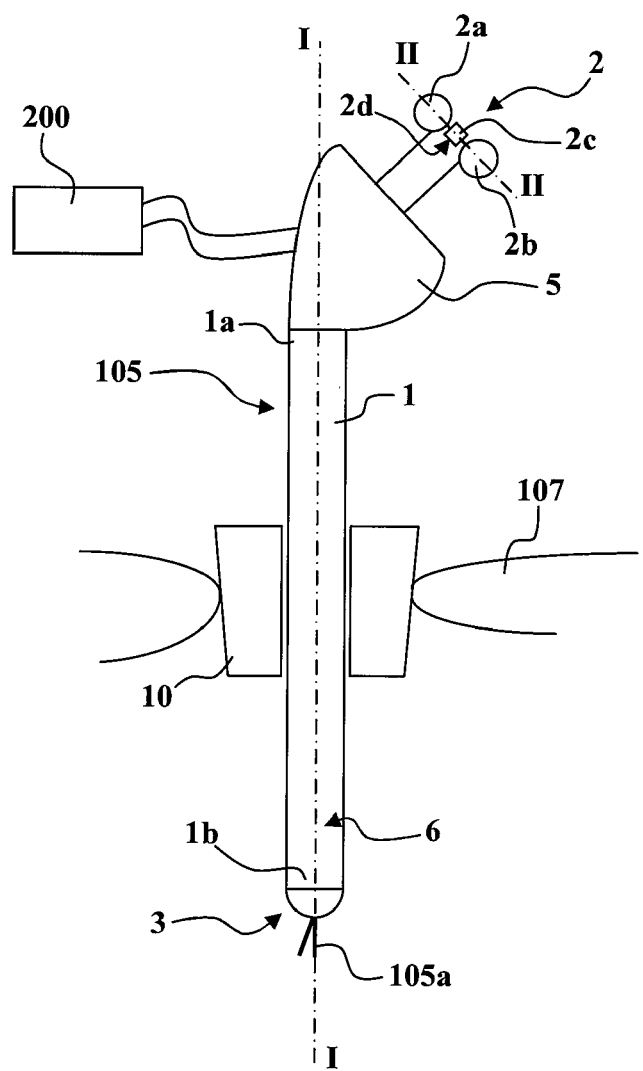
FIG. 2 is a diagrammatic side view of a manipulator of one embodiment of the present invention.

Consider next the FIG. 2 diagram, which shows in more detail the general structure of a manipulator 105 of one embodiment of the invention in a position in which it passes through the skin 107 of the patient in order to perform a surgical operation.

The manipulator 105 includes a main arm 1 having a proximal end 1a sand a distal end 1b, a proximal manipulator structure 2, a distal controlled structure 3 and a surgical trocar 10.

The surgical trocar 10 is engaged in a perforation in the skin 107 of the patient and forms a passage in which the main arm 1 can slide axially to perform an overall translation movement and the main arm 1 can turn in overall axial rotation about its longitudinal axis I-I.

The surgical trocar 10 can itself pivot to either side of the axis of the perforation in the skin 107 of the patient to allow overall pivoting movements of the main arm 1 about a pivot point consisting of the perforation in the skin 107 of the patient.

The proximal manipulator structure 2 includes at least two opposite contact areas 2a and 2b conformed to have two opposite parts of a hand of the operator bear on them. Stress sensors 2c are disposed in such a manner as to generate movement instructions as a function of the stresses present in a connecting structure 2d that connects the proximal manipulator structure 2 to the main arm 1 and is situated between the two opposite contact areas 2a and 2b.

The distal controlled structure 3 is carried by the distal end 1b of the main arm 1, and is mobile relative to said distal end 1b with at least two degrees of freedom in transverse relative pivoting and one degree of freedom in axial rotation on itself.

Drive means 5 supplied with power by a power supply included in power supply and control means 200 are adapted to generate movements as a function of movement instructions received from the proximal manipulator structure 2. In the embodiment shown in the figures, the power supply and control means 200 are away from the manipulator 105 to reduce its weight and bulk. Nevertheless, placing the power supply and control means 200 on the main arm 1 itself may be also envisaged if these power supply and control means 200 are sufficiently light and compact.

Mechanical transmission means 6 accommodated in the main arm 1 transmit to the distal controlled structure 3 movements produced by the drive means 5 to generate movements of the distal controlled structure 3 as a function of movement instructions received from the proximal manipulator structure 2.

Figure 3:
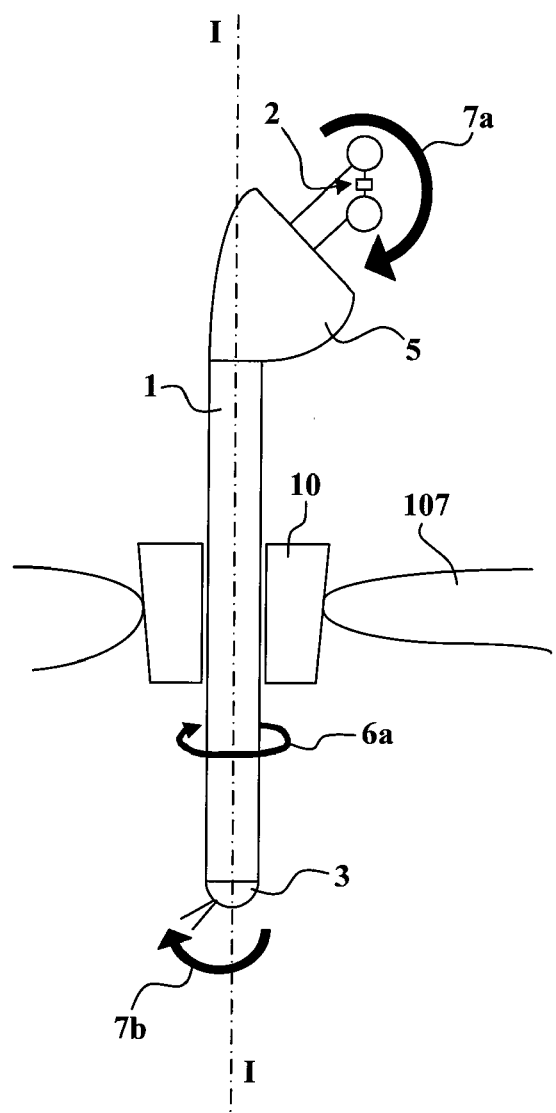
FIG. 3 shows the manipulator from FIG. 2 during a small pivoting movement of the distal controlled structure about its transverse axis.

FIG. 3 relates to a first type of movement of the distal controlled structure 3. This is a movement of relative pivoting, or of small radius pivoting relative to the main arm 1, as shown by the arrow 7b, about a distal transverse axis. This movement shown by the arrow 7b is produced by relative pivoting on itself of the proximal manipulator structure 2 with relative pivoting about a proximal transverse axis as shown by the arrow 7a. It will be noted that the distal transverse axis about which the rotation 7b of the distal controlled structure 3 may take place may have any radial orientation around the longitudinal axis I-I of the main arm 1. To this end, the proximal manipulator structure 2 is pivoted about a proximal transverse axis that may also assume any radial orientation about a longitudinal axis of the proximal manipulator structure 2. In other words, the distal controlled structure 3 has two degrees of freedom in transverse pivoting relative to the longitudinal axis I-I of the main arm 1. The figure also shows a movement of overall axial rotation 6a of the main arm 1 about its longitudinal axis I-I.

Figure 4:
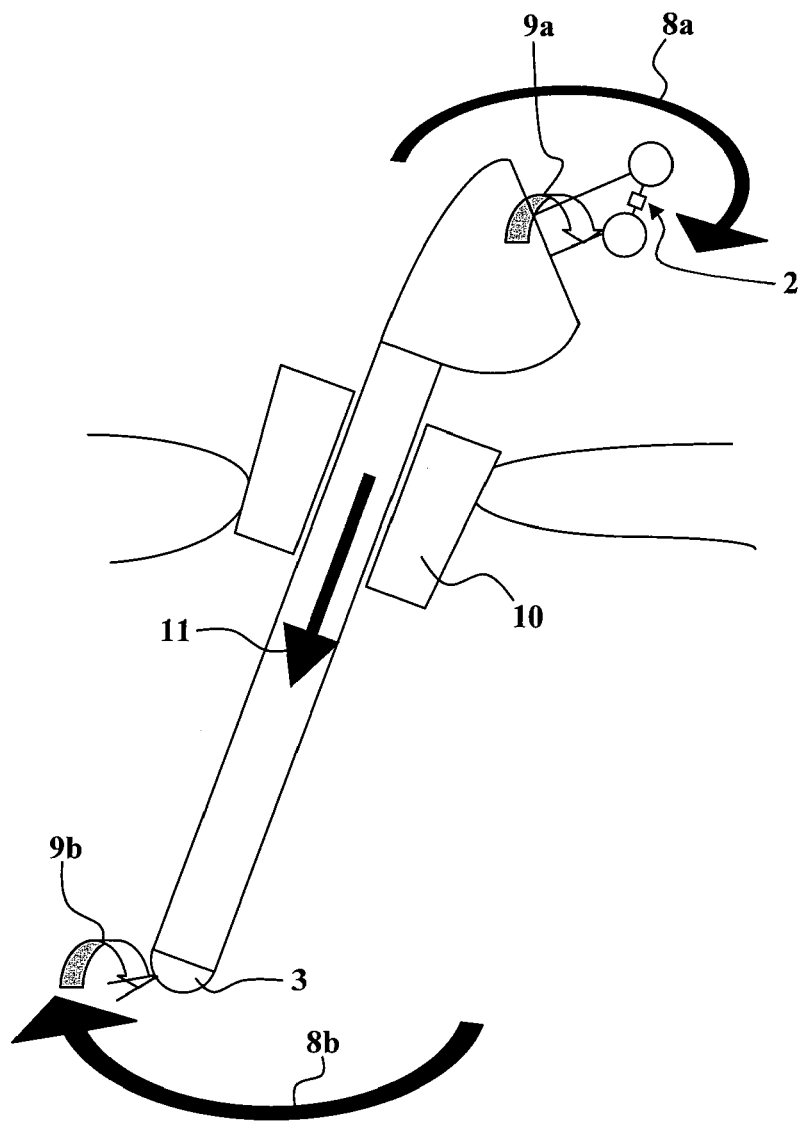
FIG. 4 shows the manipulator from FIG. 2 during a large pivoting movement about a transverse axis of the main arm and during axial rotation of the distal controlled structure.

Consider next FIG. 4, which shows two other movements of the distal controlled structure 3: on the one hand, a overall pivoting or large-radius pivoting movement, as shown by the arrow 8b, which is a rotation of the main arm 1 about a transverse intermediate axis in the area occupied by the surgical trocar 10, this overall pivoting movement being produced by a transverse stress 8a applied by the hand of the operator to the proximal manipulator structure 2 and; on the other hand, a movement of axial rotation on itself as shown by the arrow 9b, produced by a similar axial rotation on itself stress 9a applied by the hand of the operator to the proximal manipulator structure 2. FIG. 4 further shows a movement of axial overall translation of the main arm 1 in the surgical trocar 10, as shown by the arrow 11.

Such movements are necessary to produce the various surgical actions simply and ergonomically. The movements may differ in amplitude and be combined with each other as a function of the action to be performed.

Figure 5:
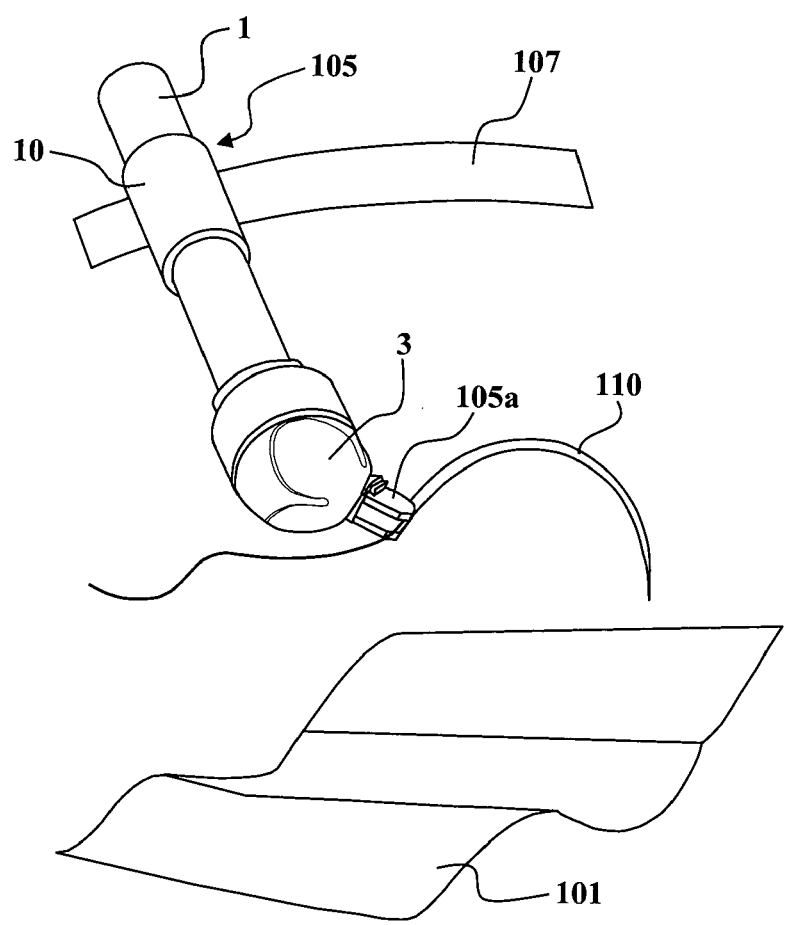
FIGS. 5, 6 and 7 show in perspective the movements of the manipulator during suturing to insert a suturing needle into tissue to be sutured.
Figure 6:
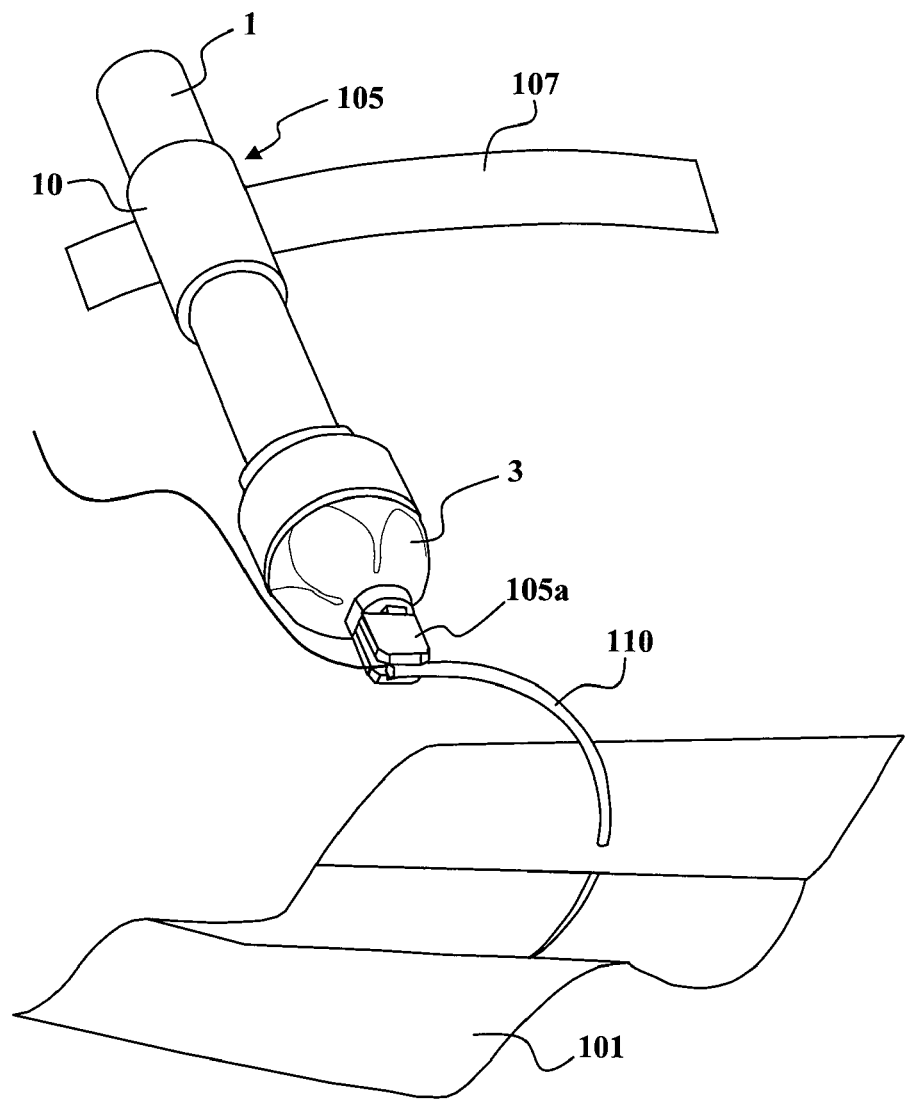
Figure 7:
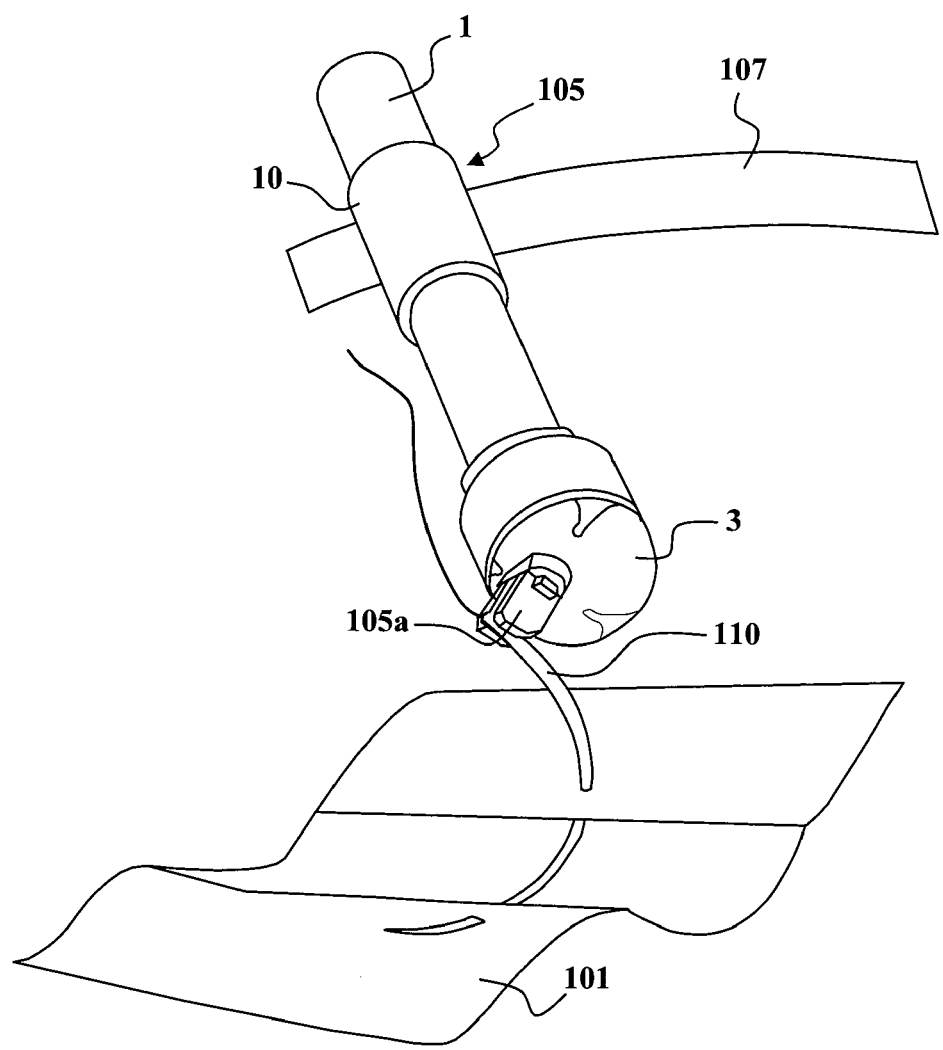

Consider by way of example FIGS. 5 to 7, which show the necessary movements for an action of passing a suture needle 110 through the tissue 101.

In this case, the distal controlled structure 3 carries a surgical tool 105a in the form of forceps with which the operator grips a proximal end of the curved suture needle 110. The operator can thus pass the curved suture needle 110 through the tissue 101 as shown in the figures by applying to the distal controlled structure 3 appropriate movements of relative pivoting, relative rotation on itself, overall pivoting, overall rotation and overall translation. It is clear that the surgical action is relatively complex and that it is entirely beneficial to simplify the movements that the operator must apply to the proximal manipulator structure 2 to perform this action.

The precision of the surgical action in particular necessitates that the movements applied by the operator to the proximal manipulator structure 2 are as natural as possible in order for everything to appear to the operator as if they were holding the curved suture needle 110 in his hand.

Figure 10:
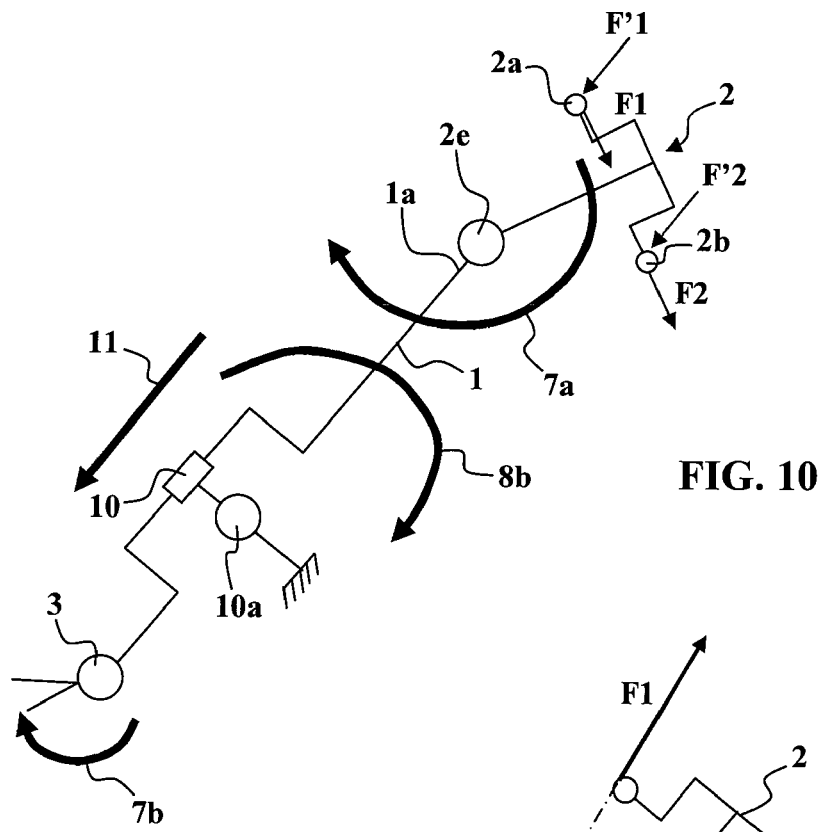
FIGS. 10 and 11 are diagrammatic views showing rotation and pivoting movements in prior art manipulators.
Figure 11:
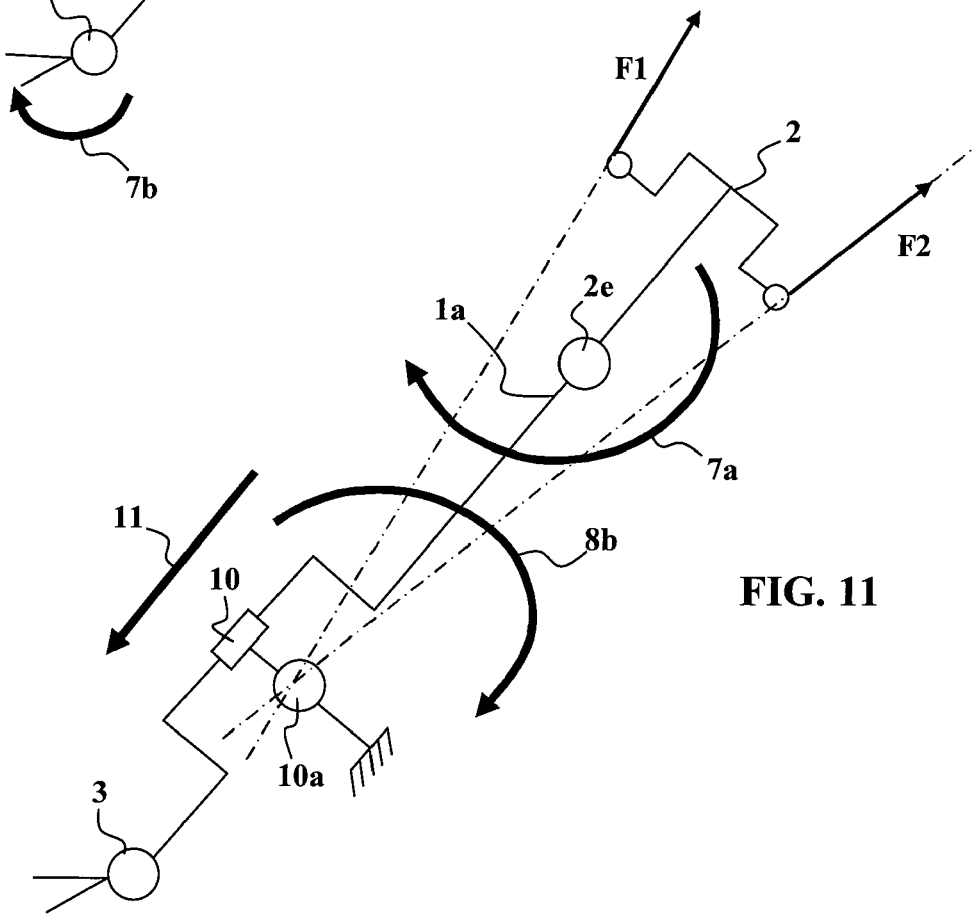
Figure 12:
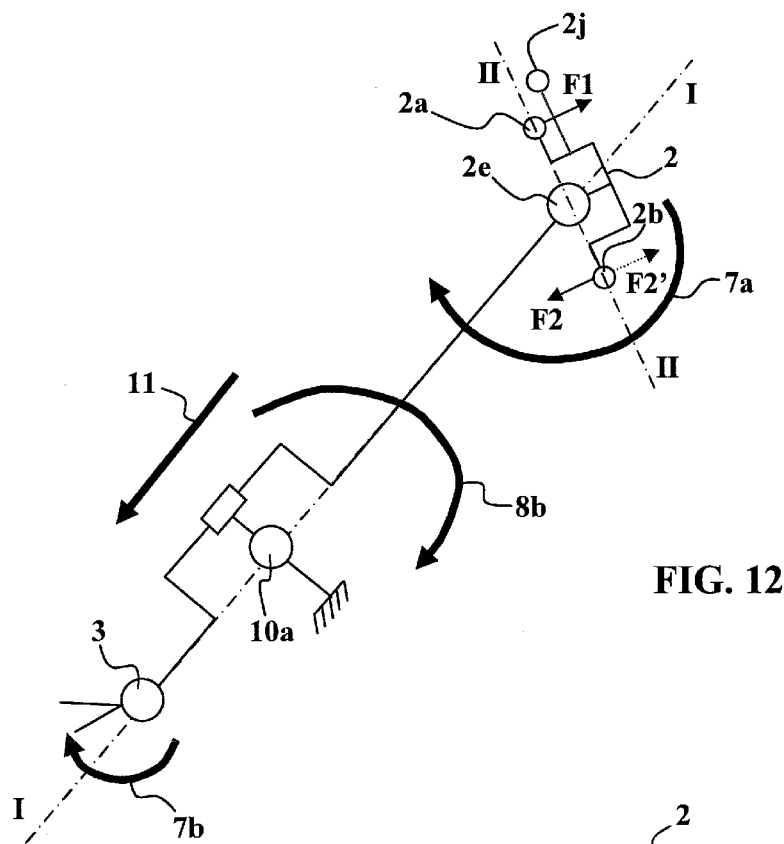
FIG. 12 shows diagrammatically pivoting and rotation movements of a manipulator of a preferred embodiment of the present invention.

To understand this difficulty, and the benefit of the invention, consider next FIGS. 10 to 12.

FIG. 10 shows a known manipulator structure, such as that described in the documents FR 2 713 129 A and FR 2 876 271 A, for example.

In this case, there are a proximal manipulator structure 2, a main arm 1, a surgical trocar 10 and a distal controlled structure 3.

The proximal manipulator structure 2 includes two offset contact areas 2a and 2b and is articulated to the proximal end 1a of the main arm 1 in an articulation type connecting area 2e, and so is adapted to pivot about the articulation 2e. The main arm 1 can pivot with the surgical trocar 10 relative to the skin of the user about a transverse pivot axis 10a.

To produce a movement of relative pivoting 7b of the distal controlled structure 3, the operator must apply to the proximal manipulator structure 2 transverse forces F1 and F2 tending to cause the proximal manipulator structure 2 to pivot about the articulation 2e. Because, in the prior art documents, the proximal manipulator structure 2 is offset away from the articulation 2e, the transverse forces F1 and F2 are in the same direction, and simultaneously induce a torque causing overall pivoting of the main arm 1 about the axis 10a. Thus the natural movement of the operator to pivot the proximal manipulator structure 2 and produce a relative pivoting movement 7b simultaneously induces a movement of overall pivoting 8b and possibly a movement of overall translation 11.

If the operator wishes to achieve a movement of pure relative pivoting 7b, they must then compensate the translation movement 11 and the overall pivoting movement 8b, which is unnatural and has to be learned, requiring continuous visual monitoring of the operating field.

To obtain pure overall translation as shown by the arrow 11, the intuitive action of the operator is to pull or push the manipulator on the axis of the main arm 1. Applying such parallel and equal forces F'1 and F'2 to the opposite contact areas 2a and 2b simultaneously produces relative pivoting of the proximal manipulator structure 2 about the articulation 2e. The operator must then correct this by modifying the direction of the applied forces or by simultaneously applying a compensation torque to the proximal manipulator structure 2, which is unnatural.

In FIG. 11, the pure overall translation shown by the arrow 11 can be obtained slightly more easily with the known devices by forces F1 and F2, but this is merely a special case in which the proximal manipulator structure 2 is on the axis of the main arm 1.

In FIG. 10, to produce an overall pivoting movement as shown by the arrow 8b, the operator must apply to the contact areas 2a and 2b forces F1 and F2 in a direction transverse to the direction of the main arm 1 to obtain pivoting thereof about the transverse axis 10a. Because the proximal manipulator structure 2 is offset away from the articulation 2e, this stress simultaneously produces a torque causing the proximal manipulator structure 2 to pivot about the articulation 2e, as shown by the arrow 7a. This stress simultaneously produces undesirable relative pivoting 7b of the distal controlled structure 3. The operator must therefore compensate this unwanted movement by simultaneously applying a compensating torque to the proximal manipulator structure 2.

Consider next FIG. 12, which shows diagrammatically the movements in a manipulator of a preferred embodiment of the present invention. In this case, the articulation 2e is situated on the longitudinal axis I-I of the main arm 1.

In all cases, the application of two equal forces F1 and F2' in the same direction to the opposite contact areas 2a and 2b does not induce any torque causing the proximal manipulator structure 2 to rotate about its articulation 2e because the two opposite contact areas are aligned with the articulation 2e. Thus stresses to produce overall pivoting about the axis 10a or overall translation 11 induce no component of relative pivoting 7a of the proximal manipulator structure 2 and of consequential relative pivoting 7b of the distal controlled structure 3.

Similarly, relative pivoting about the articulation 2e as shown by the arrow 7a is obtained by applying two equal and opposite forces F1 and F2, which does not lead to any stress in overall translation 11 or in overall pivoting 7a about the axis 10a.

To discriminate effectively the movement of axial rotation on itself of the distal controlled structure 3, this rotation movement is controlled by an additional stress sensor 2j carried by the proximal manipulator structure 2 and actuated by a free finger of the user's hand when acting on the proximal manipulator structure 2. Such a sensor 2j may be a cursor, a button, a thumbwheel, for example.

The invention thus achieves perfect dissociation of the movements, the operator being able to apply intuitive movements that normally lead to the required movements when holding a surgical instrument in the hand.

Figure 8:
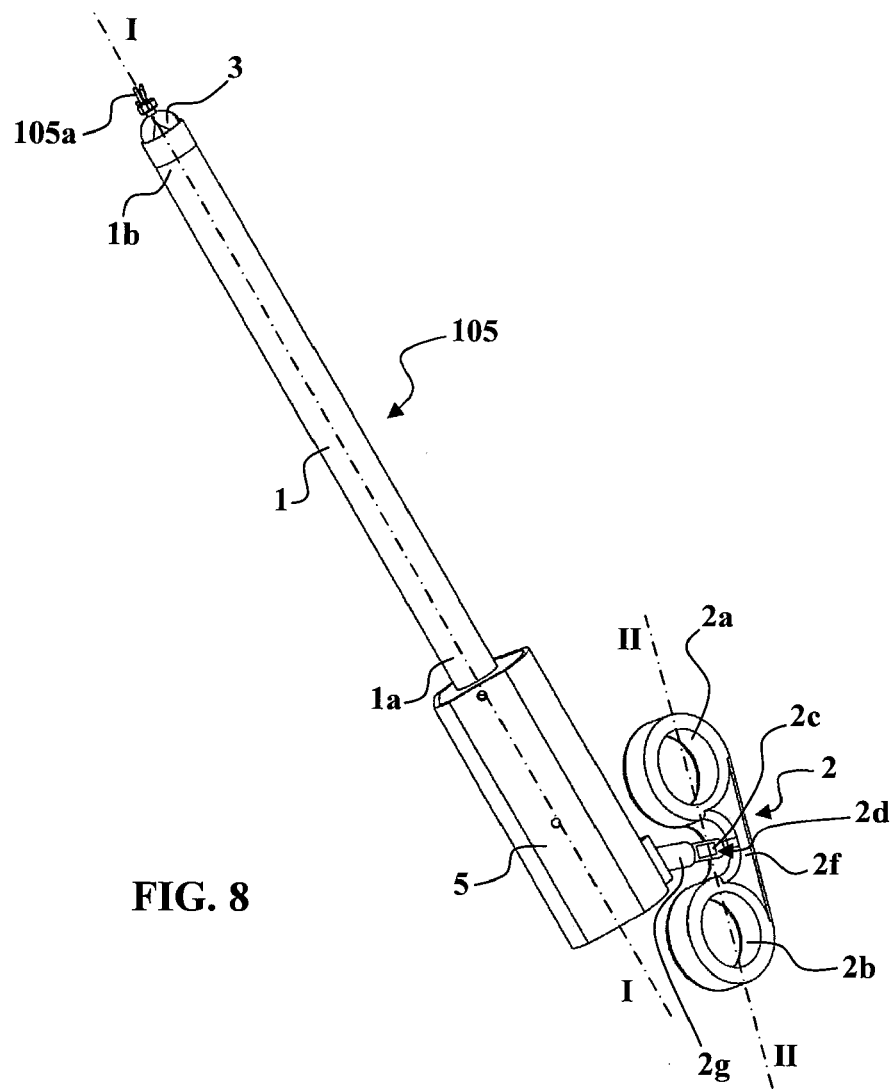
FIG. 8 is a more detailed perspective view of a manipulator of the FIG. 2 embodiment.
Figure 9:
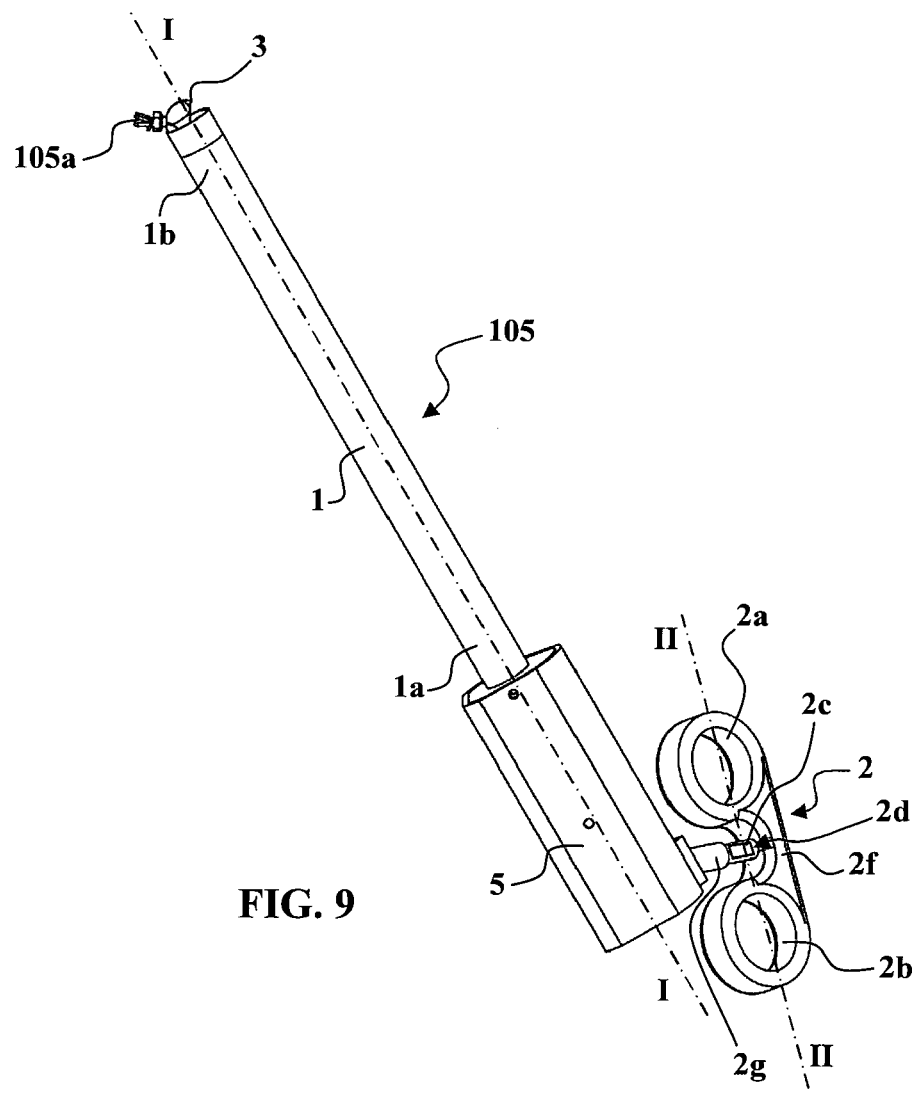
FIG. 9 is a perspective view of the manipulator from FIG. 8 in a position with a different orientation of the distal controlled structure.

Consider next FIGS. 8 and 9 which show in perspective a manipulator structure of another embodiment of the invention.

These figures include the essential parts of the manipulator from FIGS. 2 to 4, these essential parts are identified by the same reference numbers. The trocar is not shown.

There is seen at the distal end of the manipulator 105 a surgical instrument 105a in the form of forceps held by the distal controlled structure 3. In FIG. 8, the surgical instrument 105a is on the axis of the main arm 1. In FIG. 9, the surgical instrument 105a has pivoted relative to the main arm 1.

These figures show an advantageous embodiment of a proximal manipulator structure 2.

This proximal manipulator structure 2 comprises two coplanar rings constituting the opposite contact areas 2a and 2b, conformed so that the operator can pass a finger through each of the two rings 2a and 2b.

The user preferably inserts a thumb into one of the rings and a finger of the same hand into the other ring.

The rings 2a and 2b are connected by a crosspiece 2f which is itself connected to the drive means 5 and to the main arm 1 by a connecting arm 2g. The crosspiece 2f and the connecting arm 2g form a structure that carries the rings or opposite contact areas 2a and 2b. An intermediate area of the connecting arm 2g constitutes the central connecting structure 2d in which it is required to sense the stresses applied by the operator. The connecting arm 2g is oriented in a radial direction or at least strongly inclined relative to the longitudinal axis I-I of the main arm 1 so that the rings 2a and 2b are offset radially away from the main arm 1 and the rings 2a and 2b are aligned in a direction II-II at an angle of approximately 45° to the axis I-I.

According to a first possibility, the connecting structure 2d of the arm 2g is an articulated area and the sensors 2c are then movement sensors, for example encoders or potentiometers, adapted to evaluate the relative pivoting of the two successive sections of the connecting arm 2g relative to each other to produce the movement instructions. Accordingly, in this embodiment, the sensors 2c are in the connecting structure 2d itself.

According to another possibility, the connecting structure 2d of the connecting arm 2g is an elastically deformable structure, the sensors then being strain gauges 2c sensitive to deformation of this connecting structure 2d.

Placing the strain gauges away from the centre of the connecting structure 2d may also be considered, combined with correcting the strains measured by the sensors 2c in an offset area by calculation to evaluate the strains present in the intermediate area 2d.

Figure 13:
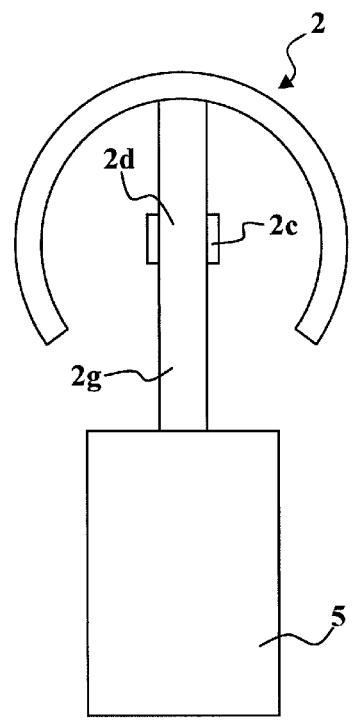
FIGS. 13 and 14 are diagrammatic side views showing two embodiments of stress sensors for the proximal manipulator structure.
Figure 14:
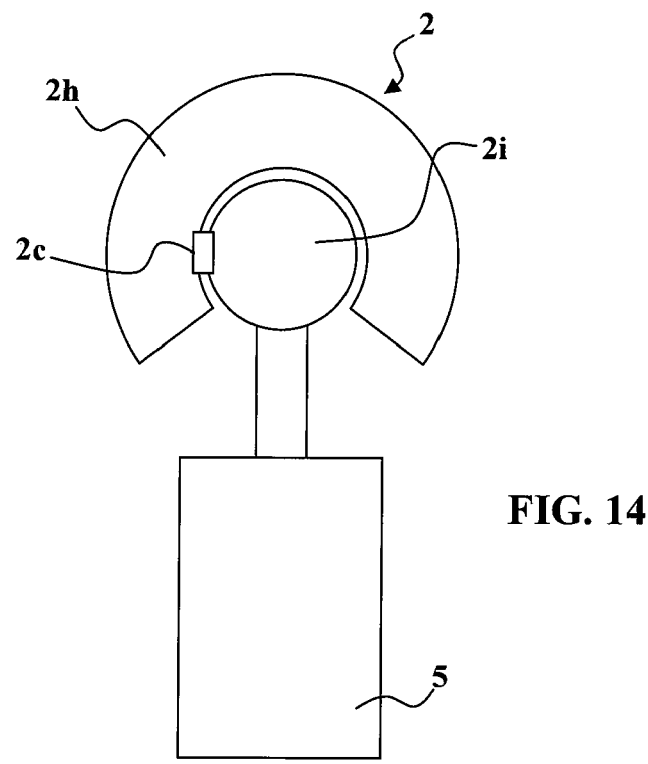
Figure 15:
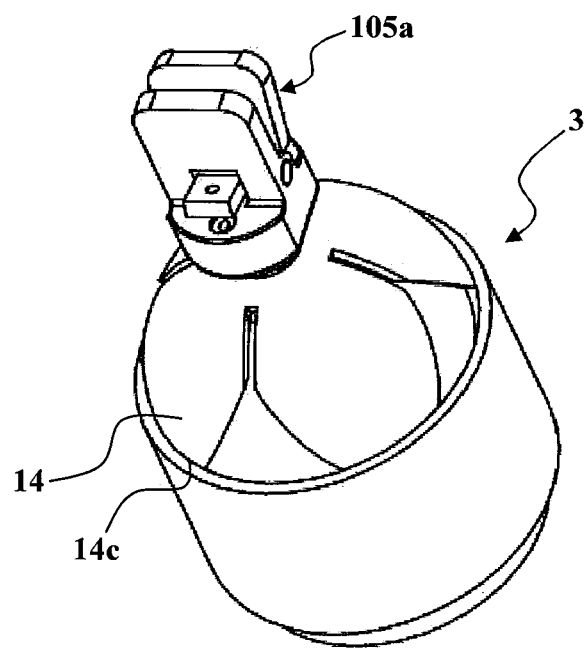
FIG. 15 is a perspective view of a distal controlled structure of one particular embodiment of the present invention.

Consider next FIGS. 13 and 14, which show two other embodiments of the proximal manipulator structure 2.

In these two embodiments the proximal manipulator structure 2 has a convex, for example spherical, external surface two diametrically opposite portions of which constitute the opposite contact areas, the operator being able to apply his hand to the external surface of the structure.

In FIG. 13, the convex structure is connected to the drive means 5 by a non-articulated connecting arm 2g the intermediate area 2d of which is elastically flexible and includes strain gauges 2c.

In FIG. 14, a peripheral sphere 2h can pivot about a central ball-joint 2i and movement sensors 2c determine movements of the peripheral sphere 2h around the central ball-joint 2i to generate the movement instructions.

Consider next FIGS. 15 to 19, which show more specifically an advantageous embodiment of the distal controlled structure 3.

The object of this particular structure is to allow relative pivoting movements of large amplitude, possibly up to approximately 70° inclination on either side of the longitudinal axis I-I of the main arm 1.

Another object of the structure is to enable this pivoting by centered rotation, providing two degrees of freedom in pivoting about two intersecting transverse axes. In other words, the distal controlled structure 3 enables regular and precise inclination of a surgical tool 105a in all directions all around the longitudinal axis I-I of the main arm 1.

Another object of this structure is to enable simultaneously axial rotation of the surgical tool 105a on itself about its longitudinal axis, independently of the relative pivoting movements on either side of the longitudinal axis I-I of the main arm 1.

This provides three degrees of freedom that are independent of each other, namely two degrees of freedom in relative pivoting about intersecting transverse axes and one degree of freedom in axial rotation of the surgical tool 105a on itself.

Moreover, the distal controlled structure 3 enables good proportionality of the movements of each of the three degrees of freedom relative to the corresponding stresses applied to the proximal manipulator structure 2.

In this embodiment shown in FIGS. 15 to 19, the distal controlled structure 3 includes, at the distal end 1b of the main arm 1, a female articulation member 12 with a hemispherical distal cavity 13 and a male articulation member 14 in the form of a hollow hemispherical dome having a hemispherical external surface 14a and an interior void 14b wide open toward its base 14c.

The male articulation member 14 is engaged in the hemispherical distal cavity 13 of the female articulation member 12 with its interior void 14b oriented toward the hemispherical distal cavity 13.

An output shaft 15 is rotatably mounted in a radial bearing 16 of the male articulation element 14 and carries a tool 105a or a tool-holder 105b.

An input shaft 17 is rotatably mounted in an axial bearing 18 of the female articulation member 12 and is longitudinally engaged in the main arm 1.

A homokinetic transmission 19 connects the input shaft 17 to the output shaft 15 to transmit movements of axial rotation whilst allowing movements of transverse pivoting of the male articulation member 14 in the female articulation member 12.

Figure 16:
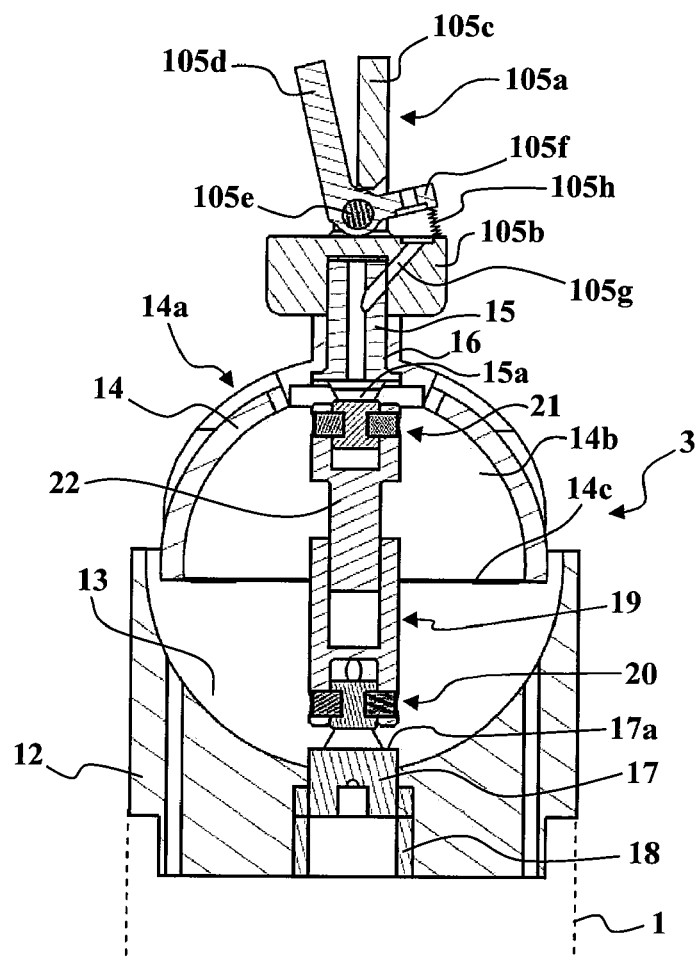
FIG. 16 is a view in longitudinal section of the distal controlled structure from FIG. 15.

In the embodiment shown in FIG. 16, the homokinetic transmission 19 includes a proximal universal joint 20 mounted at the interior end 17a of the input shaft 17, a distal universal joint 21 mounted at the interior end 15a of the output shaft 15 and a telescopic transmission shaft 22 that connects the distal end universal joint 21 to the proximal universal joint 20. The universal joints 20 and 21 are offset angularly by 90°, as shown in the figure, and are equidistant from the central axis of the spherical articulation consisting of the female articulation member 12 and the male articulation member 14.

Alternatively, the two universal joints (20-21) may be replaced by a tripod joint also providing homokinetic transmission.

In the embodiment shown in this same FIG. 16, it is seen that the surgical tool 105a is a forceps with two jaws 105c and 105d, the jaw 105d being mobile about a transverse axis 105e to produce a clamping effect.

In the embodiment shown, the mobile jaw 105d may be loaded by a traction cable, not shown, attached to a transverse arm 105f and passing through passages such as the passage 105g as far as the drive means, with a return spring 105h urging the mobile jaw 105d toward the spread apart position.

Alternatively, a shape memory alloy tool 105a may be envisaged that can assume the clamped and open positions as a function of a temperature determined by a heat source controlled by the drive means.

Figure 17:
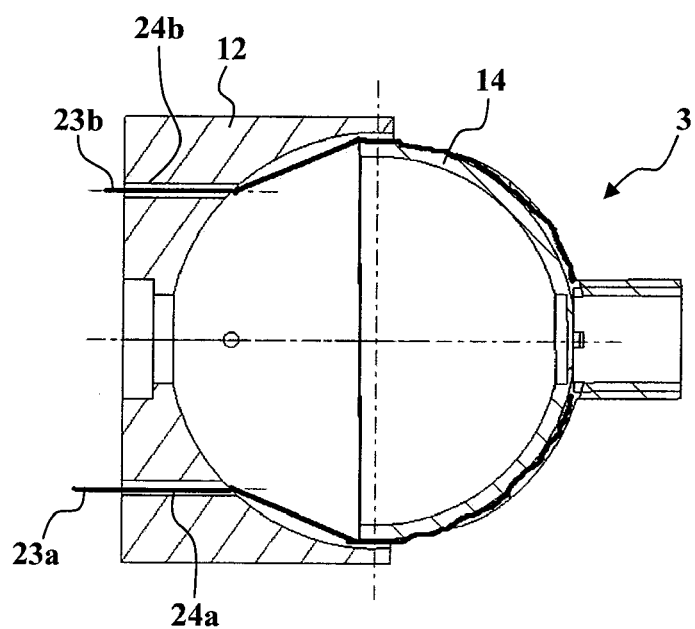
FIG. 17 is a diagrammatic view in longitudinal section of the structure from FIG. 16 in a centered position.
Figure 18:
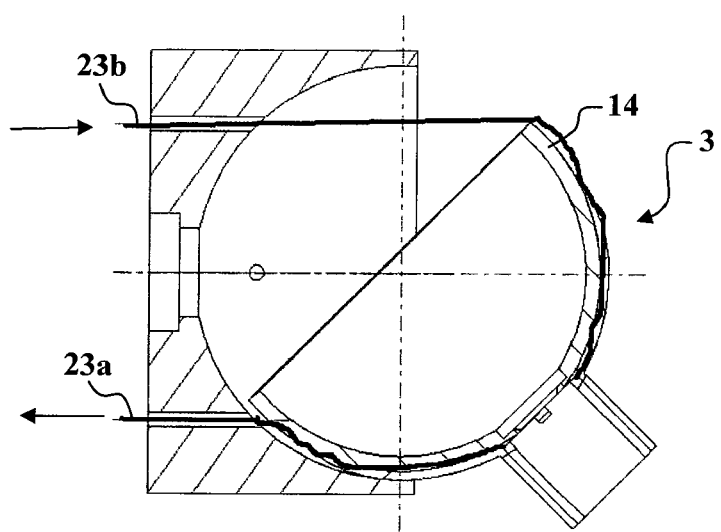
FIG. 18 is a longitudinal section of the structure from FIG. 16 in an intermediate pivoting position.
Figure 19:
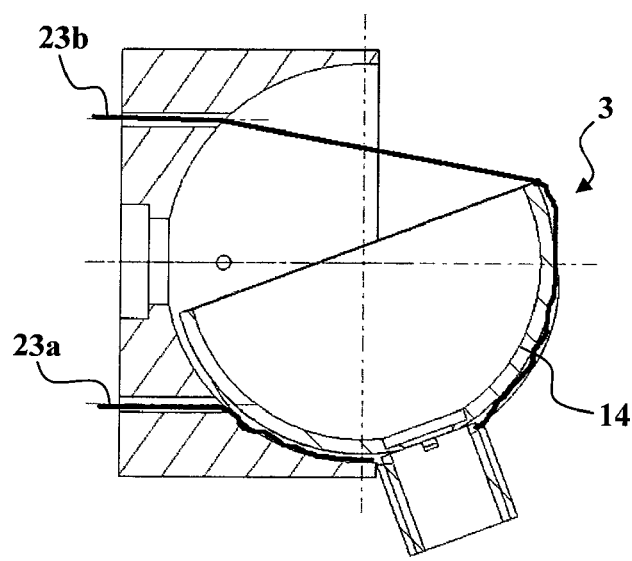
FIG. 19 is a longitudinal section of the structure from FIG. 16 in an extreme pivoting position.

As seen in FIGS. 17 to 19, a plurality of control lines, such as the lines 23a and 23b, extend inside the main arm 1 and are engaged at the periphery of the hemispherical external surface 14a of the male articulation member 14, to which peripheral surface they are fixed.

At their other end, the control lines are mechanically coupled to the drive means 5 (FIG. 8), which are themselves adapted to apply traction selectively to the control lines 23a, 23b. The drive means 5 are supplied with power by an electronic control device which can advantageously include filter means or smoothing means for producing regular traction on the control lines 23a and 23b and thus prevent the transmission of any trembling of the operator.

Where they enter the female articulation member 12, the control lines such as the lines 23a and 23b pass through respective peripheral longitudinal guide passages 24a and 24b which guide them in order to guide axial rotation of the male articulation member 14. The guide passages 24a and 24b are preferably as close as possible to the peripheral surface of the female articulation member 12. On the male articulation member 14, the control lines, such as the lines 23a and 23b, are engaged on the spherical surface of the male articulation member 14.

In practice, in the drive means 5, the control lines 23a and 23b are loaded by linear actuators controlled by a control device. For example, the diametrally opposite control lines 23a and 23b may be coupled two-by-two with a proximal return pulley and with an actuator commanding the simultaneous translation of the two control lines 23a and 23b in opposite directions (FIG. 18).

In FIG. 18, the simultaneous movement in translation in opposite directions of the control lines 23a and 23b has brought about relative pivoting by approximately 45° of the male articulation member 14. In FIG. 19, the relative pivoting has been accentuated, up to a maximum of about 70 degrees.

The distal area of the main arm 1, including the distal controlled structure 3, may advantageously be enveloped by a flexible sheath, for example in a thin and flexible polymer, allowing the surgical tool to protrude.

Figure 20:
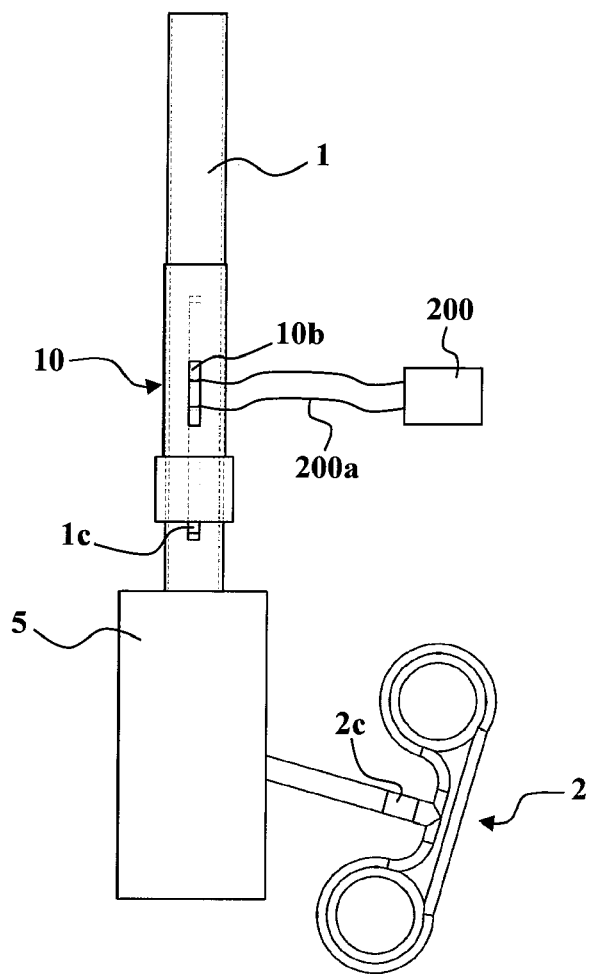
FIG. 20 is a diagrammatic side view of a manipulator of the invention with a surgical trocar.
Figure 21:
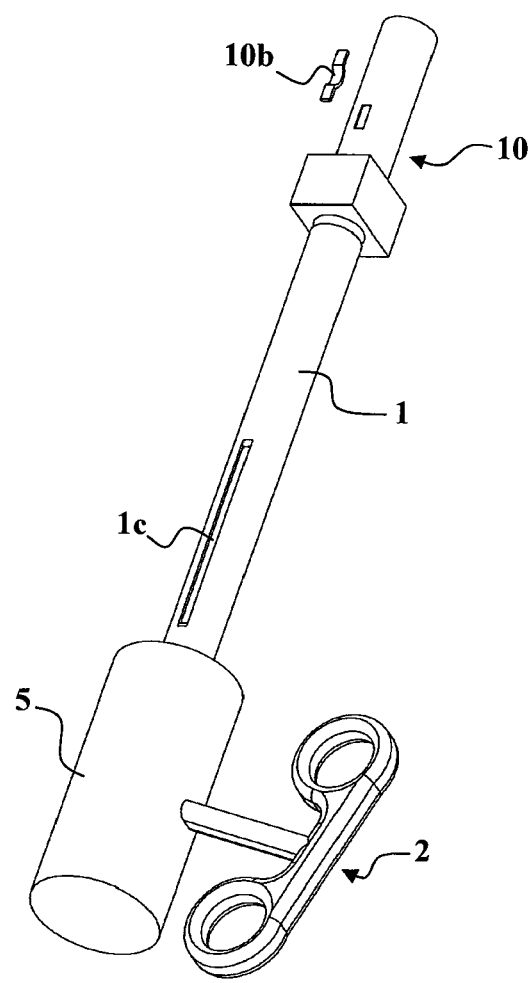
FIG. 21 shows the manipulator from FIG. 20 in perspective in a disassembled state.
Figure 22:
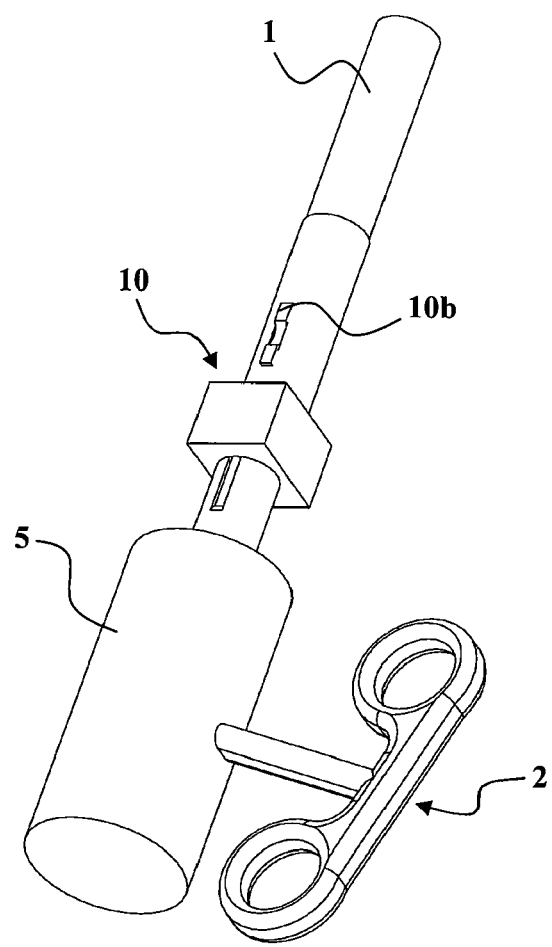
FIG. 22 shows the manipulator from FIG. 21 in an assembled state.

Consider next FIGS. 20 to 22, which show a particularly advantageous structure of a manipulator with surgical trocar 10.

The object of this structure is to reduce significantly the weight and the bulk of the manipulator itself by moving away the power supply means and the signal processing means.

For this, the surgical trocar 10 is a tubular member including sliding contact means 10b electrically connected to external power supply and control means 200 including an electrical power supply and signal processing means.

Thus the electrical conductors 200a include power conductors and signal conductors.

The sliding contact means 10b are connected to a multiple conductive track 1c of the main arm 1, which conductive track is connected on the one hand to the drive means 5 to supply electrical power to the drive means 5 and on the other hand to stress sensors 2c of the proximal manipulator structure 2.

The present invention is not limited to the embodiments explicitly described and includes variants and generalizations thereof within the scope of the following claims.

The invention claimed is:

1. Manipulator, comprising:
   a main arm having a proximal end and a distal end,
   a proximal manipulator structure carried by the proximal end of the main arm, to which it is connected by a connecting structure, having at least two opposite contact areas conformed to have two opposite parts of a hand of an operator bear on them, and including sensors adapted to generate movement instructions as a function of the stresses applied by the hand of the operator, a distal controlled structure, carried by the distal end of the main arm and mobile relative to said distal end with at least two degrees of freedom in transverse relative pivoting and one degree of freedom in axial rotation on itself, drive means supplied with power by a power supply and adapted to generate movements as a function of movement instructions received from said sensors of the proximal manipulator structure, and mechanical transmission means accommodated in the main arm, mechanically coupled to the drive means and adapted to transmit movements of the drive means to the distal controlled structure to generate the movements of the distal controlled structure as a function of the movement instructions coming from said sensors of the proximal manipulator structure, wherein:

the connecting structure is disposed in an intermediate area substantially along a line joining the opposite contact areas of the proximal manipulator structure, and at least two of said sensors are disposed in said connecting structure and adapted to generate the instructions for movement of the distal controlled structure relative to the main arm with at least two degrees of freedom of movement as a function of the stresses detected in said connecting structure.

2. Manipulator according to claim 1, wherein the connecting structure includes an articulation and the sensors are displacement sensors sensitive to the relative displacement of the main arm and the proximal manipulator structure on either side of the articulation.

3. Manipulator according to claim 1, wherein the connecting structure is an elastically deformable structure and the sensors are strain gauges sensitive to deformation of the connecting structure.

4. Manipulator according to claim 1, wherein:

the proximal manipulator structure is offset radially away from the longitudinal axis of the main arm, the opposite contact areas are, in a median position, aligned in a direction at an angle of approximately 45° to the longitudinal axis of the main arm, and the sensors disposed in the connecting structure are adapted to generate the instructions for movement of the distal controlled structure in accordance with the two degrees of freedom in relative transverse pivoting and the one degree of freedom in axial rotation on itself.

5. Manipulator according to claim 1, wherein:

the connecting structure is centered on the longitudinal axis of the main arm, the sensors disposed in the connecting structure are adapted to generate the instructions for movement of the distal controlled structure in accordance with the two degrees of freedom of movement in relative transverse pivoting, and the movements of axial rotation on itself of the distal controlled structure are commanded by the movement instructions generated by an additional stress sensor carried by the proximal manipulator structure and adapted to be actuated by a finger of the user acting on the proximal manipulator structure.

6. Manipulator according to claim 1, wherein the proximal manipulator structure includes a convex external surface two diametrically opposed portions of which constitute said opposite contact areas.

7. Manipulator according to claim 1, wherein the proximal manipulator structure includes two coplanar rings constituting said opposite contact areas connected by a crosspiece.

8. Manipulator according to claim 1, including an intermediate bearing member for the main arm in which the main arm can slide axially and which can pivot with a spherical overall pivoting movement.

9. Manipulator according to claim 8, wherein the main arm may further have a movement of overall axial rotation relative to the intermediate bearing member.

10. Manipulator according to claim 8, wherein the intermediate bearing member is a surgical trocar having contact means with sliding contacts for transmitting electrical power and signals between the main arm and an external power supply and processing system.

11. Manipulator according to claim 1, wherein the distal controlled structure comprises a distal support articulated to the end of the main arm, adapted to oscillate on either side of the longitudinal axis of the main arm in relative pivoting movement with two degrees of freedom about intersecting transverse axes and carrying a tool-holder rotary shaft adapted to turn in axial rotation on itself on the distal support.

12. Manipulator according to claim 11, wherein the sensors, the drive means and the mechanical transmission means are adapted so that:

a stress for centered relative pivoting applied to the proximal manipulator structure produces similar relative pivoting of the distal support of the distal controlled structure, and a stress for axial rotation on itself applied to the proximal manipulator structure produces similar relative axial rotation of the tool-holder rotary shaft.

13. Manipulator, comprising:

a main arm having a proximal end and a distal end, a proximal manipulator structure carried by the proximal end of the main arm, to which it is connected by a connecting structure, having at least two opposite contact areas conformed to have two opposite parts of a hand of an operator bear on them, and including sensors adapted to generate movement instructions as a function of the stresses applied by the hand of the operator, a distal controlled structure, carried by the distal end of the main arm and mobile relative to said distal end with at least two degrees of freedom in transverse relative pivoting and one degree of freedom in axial rotation on itself, drive means supplied with power by a power supply and adapted to generate movements as a function of movement instructions received from said sensors of the proximal manipulator structure, and mechanical transmission means accommodated in the main arm, mechanically coupled to the drive means and adapted to transmit movements of the drive means to the distal controlled structure to generate the movements of the distal controlled structure as a function of the movement instructions coming from said sensors of the proximal manipulator structure, wherein:

the connecting structure is disposed in an intermediate area between the opposite contact areas of the proximal manipulator structure, and at least two of said sensors are disposed in said connecting structure and adapted to generate the instructions for movement of the distal controlled structure relative to the main arm with at least two degrees of freedom of movement as a function of the stresses detected in said connecting structure, wherein the distal controlled structure includes:

at the distal end of the main arm, a female articulation member with a hemispherical distal cavity, a male articulation member in the form of a hollow hemispherical flange having a hemispherical external surface and an interior void wide open toward its base, the male articulation member being engaged in the distal hemispherical cavity of the female articulation member with its interior void oriented toward the distal hemispherical cavity, a plurality of control lines extending in the main arm, mechanically coupled to the drive means and engaged at the periphery of the hemispherical external surface of the male articulation member to command pivoting thereof by traction on the control lines, an output shaft rotatably mounted on a radial bearing of the male articulation member and carrying a tool or a toolholder, an input shaft mounted to rotate in an axial bearing of the female articulation member and engaged longitudinally in the main arm, and a homokinetic transmission that connects the input shaft to the output shaft, allowing movements of transverse pivoting of the male articulation member in the female articulation member.

14. Manipulator according to claim 13, wherein the control lines pass through peripheral longitudinal guide passages on entry into the female articulation member.

* * * * *